United States Patent [19]

Vandoni

[11] Patent Number: 4,542,141

[45] Date of Patent: Sep. 17, 1985

[54] COMPOUND HAVING VASODILATING, ANTIAGGREGATING AND HYPOCHOLESTEROLEMIC ACTIVITIES, PROCESS FOR THE PREPARATION THEREOF AND PHARMACEUTICAL COMPOSITIONS THEREFROM

[75] Inventor: Guido Vandoni, Correzzana, Italy

[73] Assignee: Edmond Pharma s.r.l., Paderno Dugnano, Italy

[21] Appl. No.: 539,839

[22] Filed: Oct. 7, 1983

[30] Foreign Application Priority Data

Oct. 15, 1982 [IT] Italy ................................ 23770 A/82

[51] Int. Cl.$^4$ .................... C07D 401/12; A61K 31/44
[52] U.S. Cl. .................................... 514/341; 546/279; 548/361
[58] Field of Search .......................... 546/279; 424/266

[56] References Cited

U.S. PATENT DOCUMENTS 2,798,074  7/1957  Pfister et al. .......................... 546/279
3,519,640  7/1970  Musil et al. .......................... 546/279

*Primary Examiner*—Jane T. Fan
*Attorney, Agent, or Firm*—Bucknam and Archer

[57] ABSTRACT

The compound having formula (I)

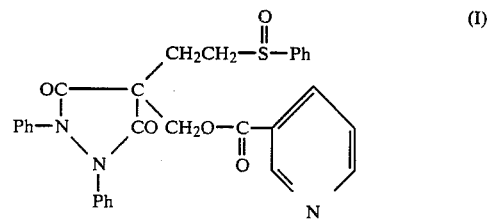

is obtained by reacting 1,2-diphenyl-4-[2-phenylsulfinyl)-ethyl]-4-hydroxymethyl-pyrazolidine-3,5-dione (hydroxymethylsulfinpyrazone) with nicotinic acid, in the presence of activating agents such as DCCD.

(I) is endowed with marked vasodilating, antiaggregating and hypocholesterolemic properties.

3 Claims, No Drawings

COMPOUND HAVING VASODILATING, ANTIAGGREGATING AND HYPOCHOLESTEROLEMIC ACTIVITIES, PROCESS FOR THE PREPARATION THEREOF AND PHARMACEUTICAL COMPOSITIONS THEREFROM

The object of the invention is provided by a new compound endowed with vasodilating, antiaggregating and hypocholesterolemic activities, namely 1,2-diphenyl-4-[2-(phenylsulfinyl)-ethyl]-4-(nicotinoyloxymethyl)-pyrazolidine-3,5-dione, having formula (I)

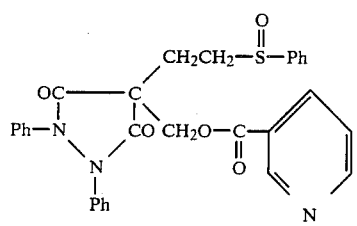

wherein Ph stands for the phenyl ring.

The invention refers moreover to a process for the preparation of compound (I), characterized in that 1,2-diphenyl-4-[2-(phenylsulfinyl)-ethyl]-4-hydroxymethyl-pyrazolidine-3,5-dione (II) is reacted with nicotinic acid (III) in the presence of dicyclohexylcarbodiimide (DCCD) (or other analogous activating agent), according to the following scheme:

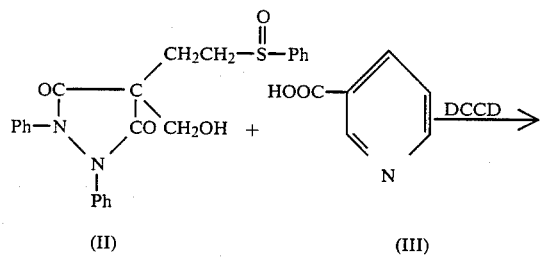

In turn, the intermediate (II) is easily accessible by reacting formaldehyde with 1,2-diphenyl-4-[2-(phenylsulfinyl)ethyl]-pyrazoline-3,5-dione, which is a commercial product known under the name of sulfinpyrazone.

The compound of formula II above, which represents the key intermediate in the preparation of the compound of the present invention, is novel and is another object of the present invention.

The vasodilating, antiaggregating and hypocholesterolemic properties of the compound of the present invention, of formula I above, allow its inclusion in pharmaceutical compositions for the treatment of cardiovascular disorders, particularly of the thrombotic or prethrombotic states of when an abnormal platelet aggregation, an abnormal cholesterol or lipid blood level or the need of a vasodilating therapy is observed.

Thus, according to another of its objects, the invention provides pharmaceutical compositions having vasodilating, antiaggregating and hypocholesterolemic activities, containing compound (I) as the active principle.

The pharmaceutical compositions of the present invention comprise the active ingredient of formula I above, alone or in admixture with a pharmaceutical carrier, in pharmaceutical forms such as tablets, coated pills, capsules, powders, granules for reconstitution into oral solutions or suspension, syrups, solutions for injectable preparations, creams, suppositories for both human and veterinary use.

The active ingredients can be alone in capsules. Otherwise they are formulated by using the common pharmaceutical carriers, such as excipients like lactose or talc, granulating agents such as magnesium stearate and stearic acid, suspending agents like methylcellulose and/or wetting agents such as polyoxyethylene stearate; preservatives like ethyl p-hydroxybenzoate and flavouring agents can also be used.

The pharmaceutical compositions of the present invention are preferably formulated in dosage unit form containing from 25 to 1000 mg of the compound of formula I above in admixture with a pharmaceutical carrier. Such unit doses can be administered once to four times daily in order to give the patient a daily dose of from 100 to 1000 mg of active ingredient.

From the pharmaco-toxicological tests described hereinafter it has been surprisingly pointed out that the compound under exam, although showing the same efficacy of the reference compounds, displayed a remarkably lower acute toxicity than the reference compounds themselves.

Moreover, from the pharmacokinetics tests carried out on the animal after oral administration in the rat, it has been shown that compound (I) (hereinafter designated also with the abbreviation VQG 582), allows to obtain a pharmacological action clearly delayed as a consequence of the activity of VQG 582 itself and of the action of its active metabolites whose activity is prolonged in time.

The following example illustrate the preparation of the compound according to the invention.

EXAMPLE 1

(a)
1,2-Diphenyl-4-[2-(phenylsulfinyl)ethyl]-4-hydroxymethyl-pyrazolidine-3,5-dione (II)

40% Formaline (25 ml) is added to a solution of 20 grams of 1,2-diphenyl-4-[2-(phenylsulfinyl)-ethyl]-pyrazolidine-3,5-dione in 120 ml of methanol. The solution, under magnetic stirring, is heated up to 50° C. for one hour and kept, always under a magnetic stirring, at room temperature for 12 hours. At the end the solvent is evaporated under reduced pressure, the residue is washed with water and extracted with dichloromethane.

The organic phase is dried on anhydrous sodium sulphate and the crude product obtained after the solvent evaporation is purified on silica gel chromatographic column, eluent ethyl acetate.

The product obtained has m.p. 144°–145° C.

Elemental analysis: for $C_{24}H_{22}N_2SO_4$ (M.W.=434): calc. % C=66.36; H=5.07; N=6.45. found % C=66.22; H=5.21; N=6.38.

The IR and NMR spectra confirm the product structure.

(b)
1,2-Diphenyl-4-[2-(phenylsulfinyl)ethyl]-4-nicotinoyloxy-methyl-pyrazolidine-3,5-dione (I)

10 g of (II) and 250 mg of 4-N,N-dimethylamino-pyridine, are added under magnetic stirring to a solution of 3.6 g of nicotinic acid in 100 ml of acetonitrile and 20 ml of dimethylsulfoxide. The solution, which is not homogeneous, is cooled and 6 g of dicyclohexylcarbodiimide, dissolved in 30 ml of acetonitrile, are added thereto.

The reaction mixture is left overnight at room temperature. At the end, the solvent is evaporated, the residue is washed with water and extracted with dichloromethane.

The organic solution is dried on anhydrous sodium sulphate and the dichloromethane is evaporated at reduced pressure. The obtained residue is crystallized from 1:1 dichloromethane-diethylether mixture; from this second crystallization 7 g of product, having m.p. 152°–154° C., are obtained.

Elemental analysis: for $C_{30}H_{25}N_3SO_5$ (M.W.=539): calc. % C=66.81; H=4.64; N=7.80. found % C=66.97; H=4.58; N=7.71.

The structure of the compound so obtained is confirmed by the IR and NMR spectra.

IR spectrum (nujol mull):

| | |
|---|---|
| 1770 cm$^{-1}$ (medium) | |
| 1735 cm$^{-1}$ (strong) | stretching C = O |
| 1710 cm$^{-1}$ (medium) | |
| 1610 cm$^{-1}$ (medium) | |
| 1040 cm$^{-1}$ (medium) | stretching S = O |
| 1030 cm$^{-1}$ (medium) | |
| 740 cm$^{-1}$ (medium) | bending arom. C—H |

NMR Spectrum (solvent CDCl$_3$, internal reference TMS): 2.35 δ, m, 2H, SO—CH$_2$—CH$_2$; 3.0 δ, m, 2H, SO—CH$_2$; 4.65 δ, s, 2H, O—CH$_2$; 7.2–7.7 δ, m, 15H aromatics; 7.7–8.2 δ, m, 1H aromatic; 8.65–8.9 δ, m, 2H aromatics; 9.1 δ, d, 1H aromatic.

EXAMPLE 2

Tablets are prepared having the following composition:

1,2-diphenyl-4-[2-(phenylsulfinyl)ethyl]-4-nicotinoyloxymethyl-pyrazolidine-3,5-dione: 400 mg
lactose: 100 mg
magnesium stearate: 20 mg.

The active ingredient is granulated with a 4% w/v aqueous solution of methylcellulose.

To the dried granules a mixture of the remainder of the ingredients is added and the final mixture is compressed into tablets.

The toxico-pharmacological characteristics of compound (I) are described hereinafter.

Acute toxicity

The study has been performed using whitish Swiss mice weighing about 20 g and Wistar rats, in the phase of weight increase, weighing about 150 g, of both sexes. The product has been administered to fasted animals (2 hours for mice and 18 hours for rats) by gastric tube (oral route) or intraperitoneal injection. Sulfipyrazone has been used as reference drug.

For the statistic calculation of LD$_{50}$ and of the respective confidence limits for p=0.05, the Probits method was followed (Finney D. J.—Probit analysis-Cambridge Univ. Press, London and New York, 1952), taking into account the death rates in the 8 days following the treatments. The obtained results are summarized in Tables I-II-III-IV.

TABLE I

Acute toxicity by the oral route in the mouse.

| Drug | sex | LD$_{50}$ mg/kg (confidence limits 95%) |
|---|---|---|
| VQG 582 | M | >4000 |
| | F | >4000 |
| sulfinpyrazone | M | 367.7 |
| | | (333.7–405.1) |
| | F | 334.9 |
| | | (281.9–397.9) |

TABLE II

Acute toxicity by the intraperitoneal route in the mouse.

| Drug | sex | LD$_{50}$ mg/kg (confidence limits 95%) |
|---|---|---|
| VQG 582 | M | 3126.9 |
| | | (2464.9–3966.6) |
| | F | 3253.6 |
| | | (2730.5–3876.0) |
| sulfinpyrazone | M | 163.4 |
| | | (143.0–210.3) |
| | F | 158.8 |
| | | (138.8–181.6) |

TABLE III

Acute toxicity by the oral route in the rat.

| Drug | sex | LD$_{50}$ mg/kg (confidence limits 95%) |
|---|---|---|
| VQG 582 | M | >4000 |
| | F | >4000 |
| sulfinpyrazone | M | 347.9 |
| | | (278.0–435.4) |
| | F | 389.5 |
| | | (328.8–461.3) |

TABLE IV

Acute toxicity by the intraperitoneal route in the rat.

| Drug | sex | LD$_{50}$ mg/kg (confidence limits 95%) |
|---|---|---|
| VQG 582 | M | 2688.7 |
| | | (2269.8–3184.9) |
| | F | 2319.3 |
| | | (1853.0–2902.9) |
| sulfinpyrazone | M | 149.1 |
| | | (129.1–172.1) |
| | F | 157.0 |
| | | (132.0–186.8) |

Pharmacological properties

Vasodilating action

Swiss male whitish mice weighing about 20 g have been used. The cutaneous temperature of the paw has been measured, in conditioned room by means of a suitable thermometric equipment, (a) for three times, at 30 minutes intervals, before treatment (basal temperature), and (b) every 30 minutes in the three hours following the drugs treatment. The drugs were administered at the dosages reported in Table V.

TABLE V

Vasodilating action in the mouse

| Drug | dose mg/kg os | mean variation of the cutaneous temperature in the 3h following the treatment | max. effect time |
|---|---|---|---|
| VQG 582 | 100 | +0.60 | 60 minutes |
| nicotinic acid | 50 | +0.75 | 30 minutes |

TABLE V-continued

| | Vasodilating action in the mouse | | |
|---|---|---|---|
| Drug | dose mg/kg os | mean variation of the cutaneous temperature in the 3h following the treatment | max. effect time |
| sulfinpyrazone | 100 | +0.05 | n.d. |

Inhibition of the thrombocytopenia induced by Arthus reaction in the guinea-pig

The method described by White and Butler (Thromb. Diath. Haemorr., 34, 533, 1975) has been used.

Male spotted guinea pigs weighing 400 g and treated as reported in the Table VI were used.

TABLE VI

| | Inhibition of the thrombocytopenia induced by the antigene-antibody Arthus reaction | | | |
|---|---|---|---|---|
| | normal animals | animals after antigenic reaction | animals after antigenic reaction treated with VQG 582 100 mg/kg os | animals after antigenic reaction treated with sulfinpyrazone 100 mg/kg os |
| N. platelets $(10^3/mm^3) \pm$ S.E. % inhibition | 275.4 23.5 | 82.5 12.5 | 218.5 19.6 70.2 | 204.3 21.4 63.1 |

"Ex vivo" platelet antiaggregating action

By this test, the effect of VQG 582, acetylsalicylic acid or sulfinpyrazone pretreatment of rabbits on the platelet aggregation induced on the PRP of these animals by 35 mcg/ml adrenaline, has been valued.

The used doses and the results obtained are reported in Table VII.

TABLE VII

| | "Ex vivo" platelet antiaggregating action | |
|---|---|---|
| Drug | dose (mg/kg os) | inhibition % |
| VQG 582 | 40 | 15 |
| | 80 | 70 |
| | 120 | 85 |
| ASA | 50 | 30 |
| | 75 | 70 |
| | 100 | 100 |

TABLE VII-continued

| | "Ex vivo" platelet antiaggregating action | |
|---|---|---|
| Drug | dose (mg/kg os) | inhibition % |
| sulfinpyrazone | 40 | 5 |
| | 80 | 30 |
| | 120 | 70 |

Hypocholesterolemic action

Whitish increasing rats of both sexes weighing about 100 g and fed with Nath's diet (Nath H., J. of Nutrit., 67, 289, 1959), randomized in lots of 10 animals each and treated according to the scheme reported in Table VIII, have been used.

The treatment lasted 40 consecutive days during which the animals have been controlled, in order to detect a toxic synthomatology or death. 24 Hours after the last administration, the survived animals have been sacrificed and the dosage of total serum cholesterol, serum triglycerides, serum phospholipids and serum free fatty acids has been performed according to the methods described by Abell et al. (J. Biol. Chem., 195, 375, 1952), VAN HANDALL et al. (J. Lab. Clin. Med., 50, 152, 1957), MORRISON (Anal. Biochem., 7, 218, 1964), DOLE AND MEINERTZ (J. Biol. Chem., 235, 2595, 1960).

The livers were withdrawn and weighed, homogenized and extracted in soxhlet. The extracted lipids, evaporated, have been weighed and expresses as % of fresh organ.

The obtained results are reported in Table VIII.

TABLE VIII

| | Hypocholesterolemic action | | | |
|---|---|---|---|---|
| parameters | normal animals | animals fed with the Nath's diet | animals fed with Nath's diet treated with VQG 582 200 mg/kg per os | animals fed with the Nath's diet treated with nicotinic acid 200 mg/kg per os |
| % dead animals | — | 40 | 10 | 10 |
| serum cholesterol mg/100 ml $\pm$ | 65.60 2.0 | 424.8 14.5 | 294.1 8.5 | 324.3 7.1 |
| serum triglycerides mg/100 ml $\pm$ | 80.0 2.3 | 168.3 2.6 | 113.8 3.4 | 134.3 3.1 |
| serum phospholipids mg/100 ml $\pm$ | 140.5 3.2 | 249.1 18.7 | 157.1 4.3 | 161.7 5.7 |
| serum free fatty acids mg/100 ml | 0.19 | 0.49 | 0.31 | 0.39 |
| liver lipids % + | 5.17 0.1 | 21.0 0.8 | 16.0 1.1 | 18.0 1.2 |

Pharmacokinetics

The study has been carried out in the rat by the oral route administering VQG 582, nicotinic acid and sulfinpyrazone at equimolar doses.

VQG 582 has been found unchanged in the plasma 30 minutes to 1 hour after the treatment, thereafter (within the first two hours) it is metabolized via an intermediate step, respectively to nicotinic acid and sulfinpyrazone.

From the bioavailability point of view the nicotinic acid treatment at equimolar doses involved a faster absorption and an AUC superimposable to VQG 582; the comparison with the sulfinpyrazone treatment has pointed out how the VQG 582 administration, always at equimolar doses, involves a prolongation of the blood concentrations expressed as sulfinpyrazone.

From these results it can be supposed that, in humans, the reduction of daily doses turnover, both with respect to nicotinic acid and sulfinpyrazone, will be allowed.

I claim:
1. 1,2-Diphenyl-4-[2-(phenylsulfinyl)ethyl]-4-(nicotinoyloxymethyl)-pyrazolidine-3,5-dione, having formula (I):

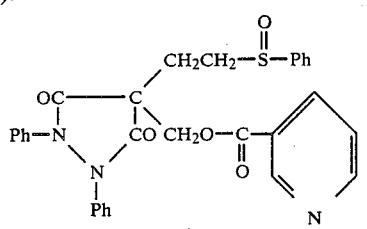

2. A pharmaceutical composition having vasodilating, antiaggregating and hypocholesterolemic activity which contain an effective amount of compound (I) as the active principle and at least one pharmaceutically acceptable carrier.

3. A pharmaceutical composition as claimed in claim 2 which is in dosage unit form and comprises from 25 to 1000 mg of active ingredient per dosage unit in admixture with a pharmaceutical carrier.

* * * * *